US012629027B2

(12) United States Patent
Tada et al.

(10) Patent No.: US 12,629,027 B2
(45) Date of Patent: May 19, 2026

(54) SYSTEM FOR MONITORING HEALTH STATUS REMOTELY

(71) Applicant: TERUMO KABUSHIKI KAISHA, Tokyo (JP)

(72) Inventors: Yuichi Tada, Santa Clara, CA (US); Yoichiro Kuwano, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 566 days.

(21) Appl. No.: 18/076,341

(22) Filed: Dec. 6, 2022

(65) Prior Publication Data

US 2023/0200648 A1 Jun. 29, 2023

(30) Foreign Application Priority Data

Dec. 29, 2021 (JP) ................................. 2021-215410

(51) Int. Cl.
*A61B 5/00* (2006.01)
*A61B 5/103* (2006.01)
(Continued)

(52) U.S. Cl.
CPC .......... *A61B 5/0022* (2013.01); *A61B 5/0053* (2013.01); *A61B 5/1032* (2013.01); *A61B 5/4875* (2013.01); *A61B 5/6831* (2013.01); *A61B 5/742* (2013.01); *G16H 10/60* (2018.01); *G16H 50/20* (2018.01); *G16H 50/30* (2018.01)

(58) Field of Classification Search
CPC ... A61B 5/0022; A61B 5/1032; A61B 5/4875; A61B 5/6831; A61B 5/742; A61B 5/6828; G16H 10/60; G16H 50/30
See application file for complete search history.

(56) References Cited

U.S. PATENT DOCUMENTS

2001/0007055 A1 7/2001 Fukuda
2008/0004904 A1* 1/2008 Tran ...................... G16H 40/67
340/286.07
(Continued)

FOREIGN PATENT DOCUMENTS

JP 4064028 A 3/2008
JP 2011-513037 A 4/2011
(Continued)

OTHER PUBLICATIONS

Notice of Reasons for Refusal mailed Jul. 1, 2025 in corresponding Japanese Patent Application No. 2021-215410, 12 pages (with Translation).

*Primary Examiner* — Carl H Layno
*Assistant Examiner* — Maria Catherine Anthony
(74) *Attorney, Agent, or Firm* — Kim & Stewart LLP

(57) ABSTRACT

A system for monitoring a health status of a person remotely from a medical facility, includes a display device to be installed in the medical facility, a wireless sensor device attachable to a leg of the person to acquire measurement information on a state of the leg of the person, and a compute server in wireless communication with the sensor device to acquire the measurement information. The compute server is configured to determine a risk of an arterial disease and a venous disease of the leg based on the acquired measurement information, and output, to the display device, information on the determined risk of the arterial disease and the venous disease of the leg.

20 Claims, 8 Drawing Sheets

100
4
6
3
1
2

(51) Int. Cl.
    *G16H 10/60*     (2018.01)
    *G16H 50/20*     (2018.01)
    *G16H 50/30*     (2018.01)

(56)          References Cited

U.S. PATENT DOCUMENTS

| | | |
|---|---|---|
| 2009/0234262 A1 | 9/2009 | Reid, Jr. et al. |
| 2013/0197340 A1* | 8/2013 | Sanders ............... A61B 5/6828 |
| | | 600/384 |
| 2017/0164876 A1* | 6/2017 | Hyde .................... A61B 5/1118 |
| 2018/0140252 A1 | 5/2018 | Luxon et al. |
| 2023/0107915 A1 | 4/2023 | Lyon et al. |

FOREIGN PATENT DOCUMENTS

| | | |
|---|---|---|
| JP | 2019-500084 A | 1/2019 |
| JP | 2021-144603 A | 9/2021 |
| WO | 2021/171226 A2 | 9/2021 |

\* cited by examiner

*FIG. 6*

ARTERIAL DISEASE

ARTERY MAY BE DISEASED

·MOISTURE CONTENT: **

START

RECEIVE VERIFICATION — S31

ASSOCIATE MEASUREMENT INFORMATION WITH INFORMATION ON RISK OF ARTERIAL DISEASE AND VENOUS DISEASE OF LEG — S32

ANONYMIZE INFORMATION — S33

RECORD MEASUREMENT INFORMATION AND INFORMATION ON RISK OF ARTERIAL DISEASE AND VENOUS DISEASE OF LEG — S34

END

SYSTEM FOR MONITORING HEALTH STATUS REMOTELY

CROSS-REFERENCE TO RELATED APPLICATION(S)

This application is based on and claims the benefit of priority from Japanese patent application No. 2021-215410, filed Dec. 29, 2021, the entire contents of which are incorporated herein by reference.

BACKGROUND OF THE INVENTION

1. Field of the Invention

Embodiments described herein relate generally to a system for monitoring a health status of a person remotely from a medical facility, a non-transitory computer readable medium storing a program for monitoring a health status of a person remotely from a medical facility, and a method for monitoring a health status of a person remotely from a medical facility.

2. Description of the Related Art

When pain occurs in a leg, a disease may be present in an artery or a vein of the leg. Moisture may stay in the leg due to a venous disease of the leg, which may result in swelling of the leg. Therefore, presence or absence of swelling is examined for disease diagnosis.

When the swelling of the leg is small, it is difficult to determine whether a cause of the pain of the leg is an arterial disease or a venous disease. That is, it is difficult to determine whether an artery is diseased or a vein is diseased simply by examining the presence or absence of the swelling.

SUMMARY OF THE INVENTION

Embodiments provide a system, a computer readable medium storing a program, and a method capable of determining a leg vascular disease.

In one embodiment, a system for monitoring a health status of a person remotely from a medical facility, includes a display device to be installed in the medical facility, a wireless sensor device attachable to a leg of the person to acquire measurement information on a state of the leg of the person, and a compute server in wireless communication with the sensor device to acquire the measurement information. The compute server is configured to determine a risk of an arterial disease and a venous disease of the leg based on the acquired measurement information, and output, to the display device, information on the determined risk of the arterial disease and the venous disease of the leg.

In one aspect, measurement information on a state of a leg of a person is acquired using a sensor device that measures a value related to the state of the leg of the person, and a risk of an arterial disease and a venous disease of the leg of the person is determined based on the measurement information. In addition, information on the determined risk of the arterial disease and the venous disease is output. It is possible to easily determine and notify of which of the artery and the vein of the leg of the person is diseased or whether neither the artery nor the vein is diseased by attaching the sensor device to the leg of the person.

With the configurations described above, it is possible to easily determine whether an artery of a leg of a person is diseased or a vein is diseased. Since the determination is easily executed, the arterial disease or the venous disease of the leg of the person can be detected at an early stage.

BRIEF DESCRIPTION OF THE DRAWINGS

FIG. 6 is a flowchart of an information output process executed by the information output system according to the first embodiment.

DESCRIPTION OF THE EMBODIMENTS

Hereinafter, embodiments will be described in detail with reference to the drawings.

First Embodiment

Figure 1:
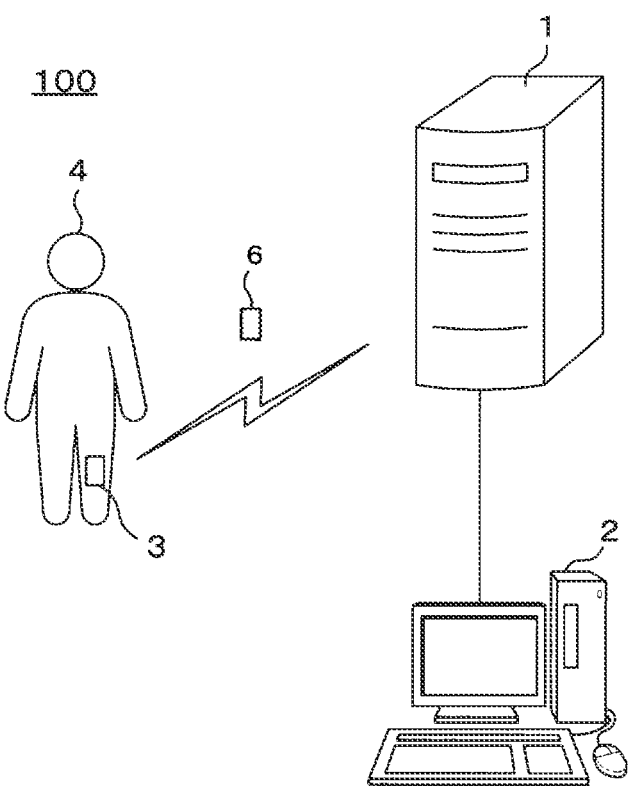
FIG. 1 is a schematic diagram illustrating a configuration of an information output system according to a first embodiment.

FIG. 1 is a schematic diagram illustrating a configuration of an information output system 100 according to a first embodiment. The information output system 100 executes an information output method for outputting information on a risk of an arterial disease and a venous disease of a leg of a person. The information output system 100 includes an information output device 1, a terminal device 2, and a sensor device 3 that measures a value related to a state of a leg of a person 4. The sensor device 3 is attached to the leg of the person 4. For example, the person 4 is a patient who visits a medical facility such as a clinic or hospital for a medical examination, and the sensor device 3 is attached to the leg of the person 4 for the examination in the clinic or hospital. For example, the sensor device 3 is attached to a calf of the leg of the person 4. The sensor device 3 transmits information indicating a measured value to the information output device 1. The information output device 1 receives the information transmitted from the sensor device 3. The information output device 1 determines the risk of the arterial disease and the venous disease of the leg of the person 4 based on the received information, and outputs the information on the risk of the arterial disease and the venous disease of the leg by transmitting the information to the terminal device 2. The terminal device 2 receives the information transmitted from the information output device 1, and displays the received information. The information output system 100 may include a plurality of terminal devices 2.

Figure 2:
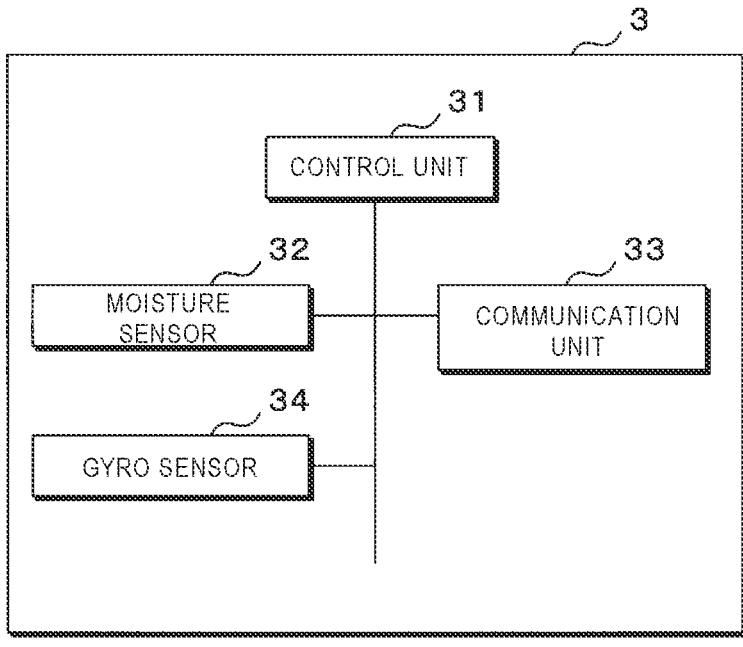
FIG. 2 is a block diagram illustrating an internal configuration of a sensor device.

FIG. 2 is a block diagram illustrating an internal configuration of the sensor device 3. The sensor device 3 measures the value related to the state of the leg of the person 4 to which the sensor device 3 is attached. The sensor device 3 includes a control unit 31, a moisture sensor 32, a communication unit 33, and a gyro sensor 34. The control unit 31 controls each unit of the sensor device 3. The moisture sensor 32 is a sensor that measures the value related to the state of the leg of the person 4. For example, the moisture sensor 32 measures a moisture content contained in a human body to which the sensor device 3 is attached. That is, the sensor device 3 measures a moisture content contained in the leg of the person 4 using the moisture sensor 32. The communication unit 33 is a network interface circuit that transmits measurement information indicating the moisture content measured by the moisture sensor 32 to the information output device 1.

In one embodiment, the sensor device 3 generates data including the measurement information obtained by the moisture sensor 32 and personal information, which is the sensor ID assigned to the sensor device 3 or the user or patient ID assigned to the user of the sensor device 3. Then, the sensor device 3 encrypts the generated data using a known encryption technique, and wirelessly transmits the encrypted data from the communication unit 33 to the information output device 11 via an access point 6 and via one or more private and/or public networks. The sensor device 3 may transmit such encrypted data via a communication line. In that case, the communication unit 33 transmits the measurement information by wired communication. The measurement information received by the information output device 1 is then transmitted to the terminal device 2.

The sensor device 3 may include a sensor other than the moisture sensor 32 for measuring the value related to the state of the leg of the person 4. That is, the sensor device 3 may acquire information other than the moisture content as the measurement information. For example, the sensor device 3 may include, in addition to or instead of the moisture sensor 32, a repulsive force sensor 35 that measures a repulsive force generated from the leg when pressure is applied to skin of the leg, a color sensor that measures a color of skin of the leg, or an infrared sensor that measures a hemoglobin amount in the human body.

Figure 3:
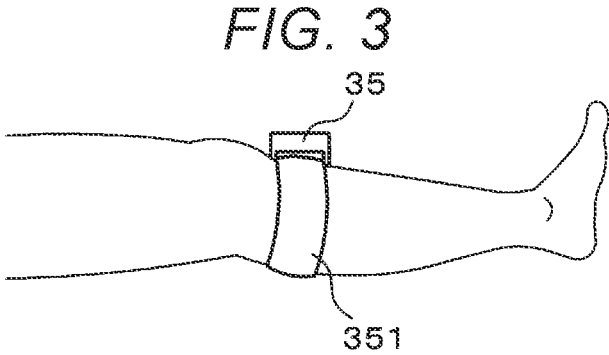
FIG. 3 is a schematic diagram illustrating a configuration of a repulsive force sensor.

FIG. 3 is a schematic diagram illustrating a configuration of the repulsive force sensor 35. The repulsive force sensor 35 is attached to a belt 351 wound around the leg of the person 4. For example, the belt 351 is wound around a calf. The repulsive force sensor 35 measures the repulsive force generated from the leg of the person 4 when the belt 351 is tightened. For example, the repulsive force sensor 35 measures, as the repulsive force, a force generated when the belt 351 is pulled in and tightened by a predetermined length from a state where the belt 351 is naturally in contact with the skin. When the repulsive force is large, the force for pulling in the belt 351 is also large, and thus the force necessary for pulling in the belt 351 can be measured as the repulsive force. The repulsive force sensor 35 may be implemented not using the belt 351. For example, the repulsive force sensor 35 may include a measurement probe for pressing the skin of the person 4, and may measure, as the repulsive force, a pressing force necessary for the measurement probe to press the skin of the person 4 to a predetermined depth.

The color sensor measures the color of skin of the leg of the person 4 by emitting light toward the skin of the leg of the person 4, detecting reflected light from the skin of the leg, and determining the color based on the detected reflected light. The color sensor may be implemented by a camera. An infrared sensor irradiates the skin of the leg of the person 4 with infrared rays, detects the infrared rays returning from the skin of the leg, and measures the hemoglobin amount at a portion of the human body to which the infrared rays are applied. The larger the hemoglobin amount is, the larger an absorption amount of the infrared rays is. The infrared sensor measures the hemoglobin amount at a portion to which the sensor device 3 is attached, that is, the hemoglobin amount at the leg of the person 4 by identifying the hemoglobin amount according to the absorption amount of the infrared rays. The communication unit 33 transmits to the information output device 1 the measurement information indicating the measured repulsive force, color of skin, and/or hemoglobin amount.

The sensor device 3 may include a plurality of types of sensors as the sensor for measuring the value related to the state of the leg of the person 4 as discussed above. For example, the sensor device 3 includes a plurality of types of sensors including the moisture sensor 32, the repulsive force sensor 35, the color sensor, and the infrared sensor. The communication unit 33 transmits a plurality of types of measurement information indicating the values measured by the plurality of types of sensors to the information output device 1.

Referring back to FIG. 2, the gyro sensor 34 is a sensor for measuring an angular velocity. For example, the gyro sensor 34 measures an angular velocity around each of three axes orthogonal to one another. The communication unit 33 transmits angular velocity information indicating the angular velocity measured by the gyro sensor 34 to the information output device 1. The gyro sensor 34 may be a sensor attached to the leg of the person 4 separately from the sensor device 3.

Figure 4:
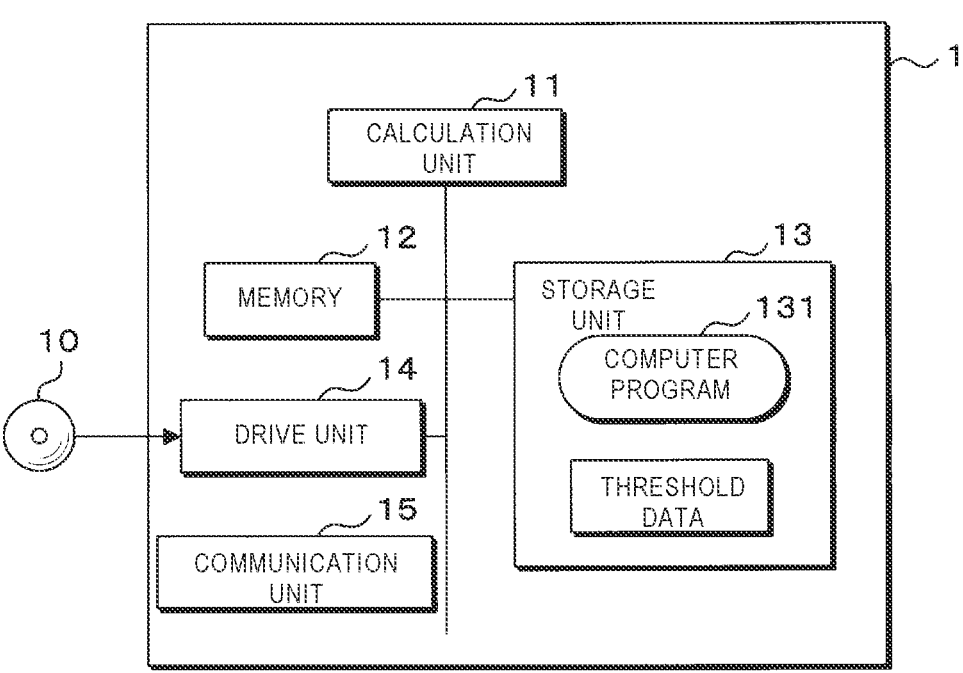
FIG. 4 is a block diagram illustrating an internal functional configuration of an information output device according to the first embodiment.

FIG. 4 is a block diagram illustrating an internal functional configuration of the information output device 1 according to the first embodiment. The information output device 1 is a computer such as a compute server installed in a medical facility such as a clinic or a hospital. The information output device 1 may be installed outside of such a medical facility, e.g., a data center. The information output device 1 includes a calculation unit 11, a memory 12 that stores temporary data generated along with calculation, a storage unit 13, a drive unit 14 that reads information from a recording medium 10 such as an optical disk or a portable memory, and a communication unit 15. The calculation unit 11 is a processor, such as a central processing unit (CPU), a graphics processing unit (GPU), or a multi-core CPU. The calculation unit 11 may be a quantum processor. The memory 12 stores the temporary data generated along with the calculation. The memory 12 is, for example, a random access memory (RAM). The storage unit 13 is nonvolatile, and is, for example, a hard disk drive or a nonvolatile semiconductor memory. The communication unit 15 is a network interface circuit that communicates with the sensor device 3 and the terminal device 2.

The calculation unit 11 causes the drive unit 14 to read a computer program 131 recorded in the recording medium 10, and causes the storage unit 13 to store the read computer program 131. The calculation unit 11 executes processing necessary for the information output device 1 according to the computer program 131. The computer program 131 may be downloaded from outside of the information output device 1 by the communication unit 15. In this case, the information output device 1 may not include the drive unit 14. The information output device 1 may be implemented by a plurality of computers.

Figure 5:
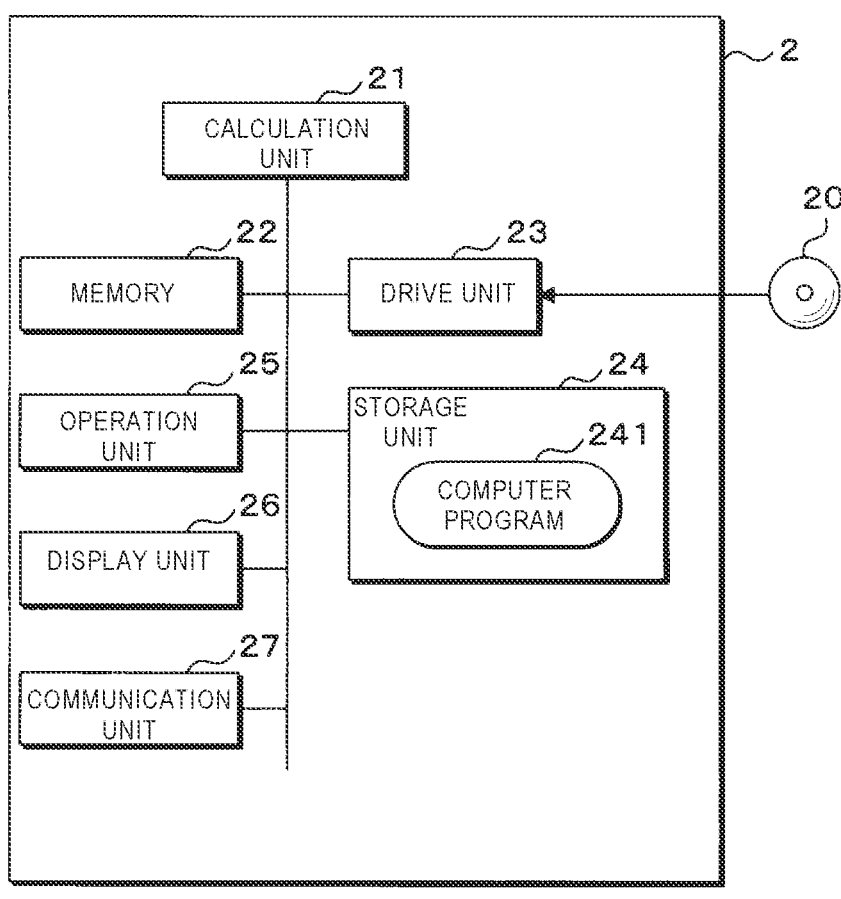
FIG. 5 is a block diagram illustrating an internal configuration of a terminal device.

FIG. 5 is a block diagram illustrating an internal configuration of the terminal device 2. The terminal device 2 is a computer such as a personal computer or a mobile terminal, e.g., a tablet computer or a smart phone. For example, a user of the terminal device 2 is a health care worker such as a medical doctor who works in a medical facility such as a clinic or a hospital. The terminal device 2 includes a calculation unit 21, a memory 22, a drive unit 23 that reads information from a recording medium 20 such as an optical disk or a portable memory, a storage unit 24, an operation unit 25, a display unit 26, and a communication unit 27. The calculation unit 21 is a processor, such as a CPU, a GPU, or a multi-core CPU. The calculation unit 21 may be a quantum processor. The memory 22 stores temporary data generated along with calculation. The memory 22 is, for example, a RAM. The storage unit 24 is nonvolatile, and is, for example, a hard disk drive or a nonvolatile semiconductor memory.

The calculation unit 21 causes the drive unit 23 to read a computer program 241 recorded in the recording medium 20, and causes the storage unit 24 to store the read computer program 241. The calculation unit 21 executes processing necessary for the terminal device 2 according to the computer program 241. The computer program 241 may be stored in the storage unit 24 in advance, or may be downloaded from outside of the terminal device 2. In this case, the terminal device 2 may not include the drive unit 23.

The operation unit 25 receives an input operation of information such as text from the user. The operation unit 25 is, for example, a touch panel. The display unit 26 displays an image. The display unit 26 may be, for example, a liquid crystal display (LCD) or an electroluminescent (EL) display. The operation unit 25 and the display unit 26 may be integrated into a touch display. The communication unit 27 is a network interface circuit that communicates with the information output device 1. The communication unit 27 may communicate with the information output device 1 via wireless communication. The communication unit 27 may communicate with the information output device 1 via a communication network such as local area network (LAN) (not illustrated), and may use wired communication.

Figure 6:
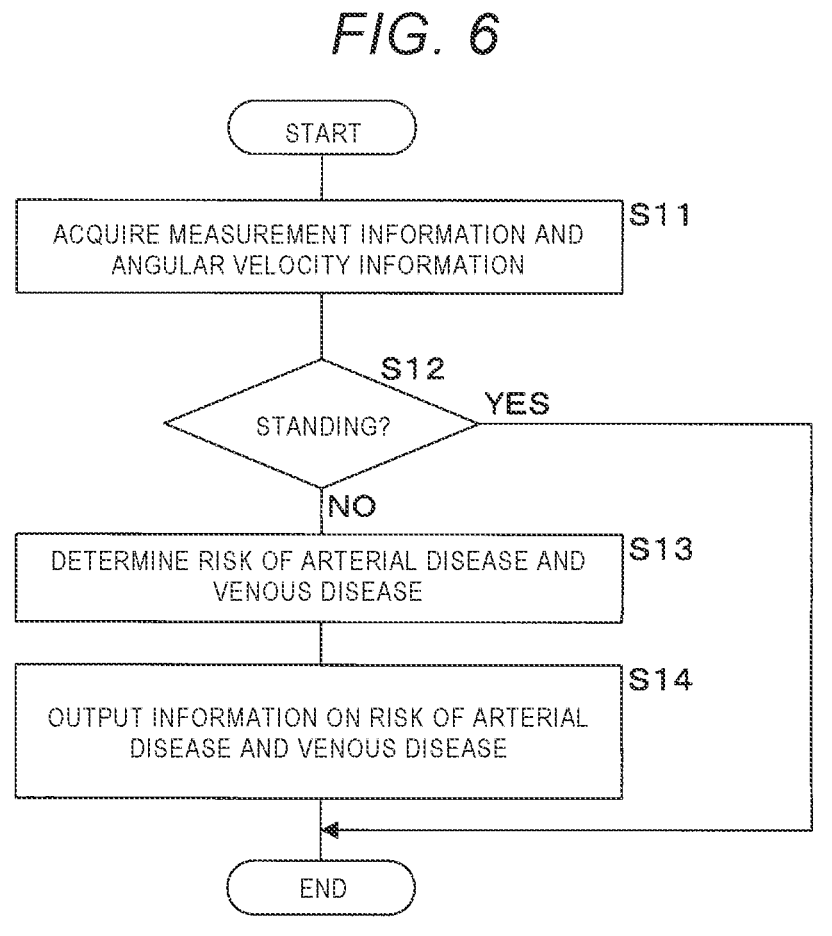

The information output system 100 outputs information on the risk of the arterial disease and the venous disease of the leg of the person 4 according to the information measured by the sensor device 3. FIG. 6 is a flowchart of an information output process executed by the information output system 100 according to the first embodiment. Hereinafter, the description of "step" will be abbreviated as "S". The calculation unit 11 of the information output device 1 executes the following process according to the computer program 131.

The information output device 1 acquires the angular velocity information and the measurement information on the state of the leg of the person 4 measured by the sensor device 3 (S11). In S11, the sensor device 3 transmits the measurement information indicating the moisture content measured by the moisture sensor 32 and the angular velocity information indicating the angular velocity measured by the gyro sensor 34 to the information output device 1. The information output device 1 receives the measurement information and the angular velocity information via the communication unit 15.

The information output device 1 determines whether the person 4 is standing based on the angular velocity information (S12). In S12, the calculation unit 11 determines whether the person 4 is standing based on the angular velocity indicated by the angular velocity information. In the state in which the person 4 is standing, the leg moves, and an absolute value of the angular velocity increases. In a state in which the person 4 is not standing, such as a state in which the person 4 is sitting or sleeping, the absolute value of the angular velocity decreases. For example, the calculation unit 11 determines that the person 4 is standing when the absolute value of the angular velocity indicated by the angular velocity information exceeds a predetermined reference value, and determines the person 4 is not standing when the absolute value of the angular velocity is equal to or less than the reference value. The calculation unit 11 may determine based on a single piece of the angular velocity information, or may determine based on an average value of a plurality of pieces of the angular velocity information acquired within a predetermined length of time.

When the person 4 is standing (S12: YES), the information output device 1 ends the process. When the person 4 is not standing (S12: NO), the information output device 1 determines the risk of the arterial disease and the venous disease of the leg of the person 4 based on the acquired measurement information (S13). The risk of the arterial disease and the venous disease is a possibility that one of the artery and the vein of the leg of the person 4 is diseased. For example, it is determined which of the artery and the vein is diseased as the determination of the risk. For example, it is possible to determine that neither the artery nor the vein is diseased as the determination of the risk. In S13, the calculation unit 11 uses the measurement information acquired substantially simultaneously with the angular velocity information which is a basis for determining that the person 4 is not standing. For example, the calculation unit 11 uses the measurement information acquired at a time closest to a time point at which the angular velocity information is acquired. For example, a time point at which the measurement is executed is attached to the measurement information and the angular velocity information. The calculation unit 11 uses the measurement information acquired at a time closest to a time point at which the angular velocity information is measured.

In S13, the calculation unit 11 compares the moisture content indicated by the measurement information with a predetermined threshold. When the artery is diseased, it is less likely to supply blood to the leg, and the moisture content contained in the leg decreases. When the vein is diseased, the blood is less likely to return from the leg to the heart, moisture stays in the leg, and the moisture content contained in the leg is large. Therefore, it is possible to determine which of the artery and the vein of the leg is diseased or whether neither the artery nor the vein is diseased based on the moisture content contained in the leg. For example, when the moisture content indicated by the measurement information is less than a predetermined first threshold, the calculation unit 11 determines that the artery of the leg of the person 4 is diseased. For example, when the moisture content indicated by the measurement information exceeds a predetermined second threshold larger than the first threshold, the calculation unit 11 determines that the vein of the leg of the person 4 is diseased. For example, when the moisture content indicated by the measurement information is equal to or greater than the first threshold and equal to or less than the second threshold, the calculation unit 11 determines that neither the artery nor the vein is diseased. The storage unit 13 stores in advance threshold data in which the first threshold and the second threshold are recorded.

In S13, the calculation unit 11 may determine which of the artery and the vein of the leg of the person 4 is diseased or whether neither the artery nor the vein is diseased according to a medical history of the person 4. According to the medical history of the person 4, ease of occurrence of the arterial disease or the venous disease of the leg is different. For example, in the person 4 undergoing cardiovascular therapy, calcification is likely to occur in the artery of the leg. In the threshold data, a first threshold and a second threshold are recorded for each medical history such as treatment history such as cardiovascular therapy, disease history such as diabetes, and a result of blood examination. For example, a first threshold having a relatively larger value is recorded in association with a medical history in which an arterial disease is likely to occur, and a second threshold having a relatively smaller value is recorded in association with a medical history in which a venous disease is likely to occur. For example, the medical history of the person 4 is stored in advance in the storage unit 13 in association with identification information on the person 4. In S11, the information output device 1 acquires the identification information on the person 4 together with the measurement information and the angular velocity information. In S13, the calculation unit 11 identifies the medical history of the person 4 according to the identification information, reads out the first threshold and the second threshold associated with identified medical history from the threshold data, and determines using the read first threshold and second threshold.

Even when the measurement information is information other than the moisture content, in S13, the calculation unit 11 can determine which of the artery and the vein of the leg of the person 4 is diseased or whether neither the artery nor the vein is diseased based on the measurement information. For example, when the measurement information indicates the repulsive force generated from the leg when the pressure is applied to the skin of the leg, the calculation unit 11 determines which of the artery and the vein of the leg of the person 4 is diseased or whether neither the artery nor the vein is diseased according to the repulsive force indicated by the measurement information. When the artery of the leg is diseased, it is less likely to supply blood to the leg, and swelling does not easily occur in the leg. In a state in which the swelling does not occur, the repulsive force generated from the leg when the pressure is applied to the skin of the leg is relatively large. When the vein is diseased, the blood is less likely to return from the leg to the heart, the moisture stays in the leg, and the swelling occurs. In a state in which the swelling occurs, when the pressure is applied to the skin of the leg, the skin is less likely to return from a deformed state, and the repulsive force is relatively small. Therefore, it is possible to determine whether the vein of the leg is diseased according to the repulsive force. For example, the calculation unit 11 determines that the vein of the leg of the person 4 is diseased when the repulsive force indicated by the measurement information is less than a predetermined threshold, and determines that the vein is not diseased when the repulsive force is equal to or greater than the predetermined threshold. The threshold is stored in the threshold data for each medical history and the calculation unit 11 may determine according to the medical history of the person 4.

Even when the measurement information indicates the color of skin of the leg, the calculation unit 11 can determine which of the artery and the vein of the leg of the person 4 is diseased or whether neither the artery nor the vein is diseased according to the color of skin of the leg indicated by the measurement information. When the artery of the leg is diseased, it is less likely to supply blood to the leg, and the color of skin of the leg becomes non-red, e.g., white. When the vein of the leg is diseased, venous blood stays in the leg. Since the venous blood has a dark red color, the color of skin of the leg becomes dark red. Therefore, it is possible to determine which of the artery and the vein of the leg is diseased or whether neither the artery nor the vein is diseased based on the color of skin of the leg. For example, when the color of skin indicated by the measurement information is whiter than a predetermined first standard color, the calculation unit 11 determines that the artery of the leg of the person 4 is diseased. For example, when the color of skin indicated by the measurement information is darker red than a predetermined second standard color, the calculation unit 11 determines that the vein of the leg of the person 4 is diseased. For example, when the color of skin is not whiter than the first standard color or not darker red than the second standard color, the calculation unit 11 determines that neither the artery nor the vein is diseased. Data that represents the first standard color and the second standard color is recorded in the threshold data in advance. The data that represents the first standard color and the second standard color is stored in the threshold data for each medical history, and the calculation unit 11 may determine according to the medical history of the person 4.

Even when the measurement information indicates the hemoglobin amount in the leg of the person 4, the calculation unit 11 can determine which of the artery and the vein of the leg of the person 4 is diseased or whether neither the artery nor the vein is diseased according to the hemoglobin amount indicated by the measurement information. When the artery of the leg is diseased, it is less likely to supply blood to the leg, and the hemoglobin amount in the leg is relatively small. When the vein of the leg is diseased, blood stays in the leg, and the hemoglobin amount in the leg is relatively large. Therefore, it is possible to determine which of the artery and the vein of the leg is diseased or whether neither the artery nor the vein is diseased based on the hemoglobin amount in the leg. For example, when the hemoglobin amount indicated by the measurement information is less than a predetermined first threshold, the calculation unit 11 determines that the artery of the leg of the person 4 is diseased. For example, when the hemoglobin amount indicated by the measurement information exceeds a predetermined second threshold larger than the first threshold, the calculation unit 11 determines that the vein of the leg of the person 4 is diseased. For example, when the hemoglobin amount indicated by the measurement information is equal to or greater than the first threshold and equal to or less than the second threshold, the calculation unit 11 determines that neither the artery nor the vein is diseased. The first threshold and the second threshold are stored in the threshold data for each medical history, and the calculation unit 11 may determine according to the medical history of the person 4.

When the sensor device 3 includes a plurality of types of sensors as the sensor for measuring the value related to the state of the leg of the person 4, the information output device 1 may execute the processing of S13 using a plurality of types of the measurement information. For example, the sensor device 3 includes a plurality of types of sensors including the moisture sensor 32, the repulsive force sensor 35, the color sensor, and the infrared sensor. In S11, the information output device 1 acquires the plurality of types of the measurement information indicating values measured by the plurality of types of sensors. In S13, the calculation unit 11 determines the risk of the arterial disease and the venous disease of the leg of the person 4 using the plurality of types of the measurement information including, for example, the moisture content, the repulsive force, the color of skin, or the hemoglobin amount. When determining that the artery or the vein is diseased using one of the measurement information, the calculation unit 11 may determine which of the artery and the vein is diseased. When determining that the artery is diseased or the vein is diseased a predetermined number of times or more as a result of determination using the plurality of types of measurement information, the calculation unit 11 may determine which of the artery and the vein is diseased. When the number of times for determining that the artery is diseased or the vein is diseased is less than the predetermined number, the calculation unit 11 may determine that neither the artery nor the vein is diseased. Alternatively, the calculation unit 11 may use different types of measurement information between when an arterial disease is determined and when a venous disease is determined, such as determining whether the vein is diseased based on the repulsive force and determining whether the artery is diseased based on the color of skin.

In S13, the information output device 1 may determine the risk of the arterial disease and the venous disease of the leg of the person 4 based on the measurement information measured a plurality of times. For example, the processing of S11 may be repeated a plurality of times, and in S13, the calculation unit 11 may determine based on an average value of a plurality of pieces of the measurement information acquired within the predetermined length of time. For example, the calculation unit 11 may determine based on a minimum value or a maximum value of the plurality of pieces of measurement information. For example, in S11, the sensor device 3 may transmit, to the information output device 1, the average value of the measurement information measured within the predetermined length of time, and in S13, the calculation unit 11 may determine based on the acquired average value.

In S13, the information output device 1 may determine a degree of disease according to the measurement information. When the arterial disease is more severe, it is further less likely to supply blood to the leg, the moisture content in the leg is smaller, the color of skin of the leg is whiter, and the hemoglobin amount in the leg is smaller. For example, a plurality of first thresholds or first standard colors are determined according to a plurality of degrees of the arterial disease, and data representing the first thresholds or the first standard colors is recorded in the threshold data in association with the degree of disease. As the degree of the arterial disease becomes severe, the first threshold becomes smaller, and the first standard color becomes whiter.

When the venous disease is more severe, the venous blood is more likely to stay in the leg, the moisture content contained in the leg becomes larger, the repulsive force generated from the leg when the pressure is applied to the skin of the leg becomes smaller, the color of skin of the leg becomes darker red, and the hemoglobin amount in the leg becomes larger. For example, a plurality of second thresholds, thresholds of the repulsive force, or second standard colors are determined according to a plurality of degrees of the venous disease, and data representing the second thresholds, the thresholds of the repulsive force, or the second standard colors is recorded in the threshold data in association with the degree of disease. As the degree of the venous disease becomes severe, the second threshold becomes larger, the threshold of the repulsive force becomes smaller, and the second standard color becomes darker red. In S13, the calculation unit 11 compares the first threshold, the data representing the first standard color, the second threshold, the threshold of the repulsive force, or the data representing the second standard color recorded in the threshold data with the measurement information, and determines the degree of disease.

After S13 is ended, the information output device 1 outputs the information on the determined risk of the arterial disease and the venous disease of the leg (S14). In S14, the calculation unit 11 controls the communication unit 15 to transmit the information on the risk of the arterial disease and the venous disease of the leg determined in S13 to the terminal device 2. The terminal device 2 receives the information on the risk of the arterial disease and the venous disease of the leg of the person 4 at the communication unit 27, and the calculation unit 21 controls the display unit 26 to display an image including the information on the risk of the arterial disease and the venous disease of the leg. For example, the information on the risk is information illustrating which of the artery and the vein of the leg of the person 4 is diseased or information illustrating whether neither the artery nor the vein is diseased.

Figure 7:
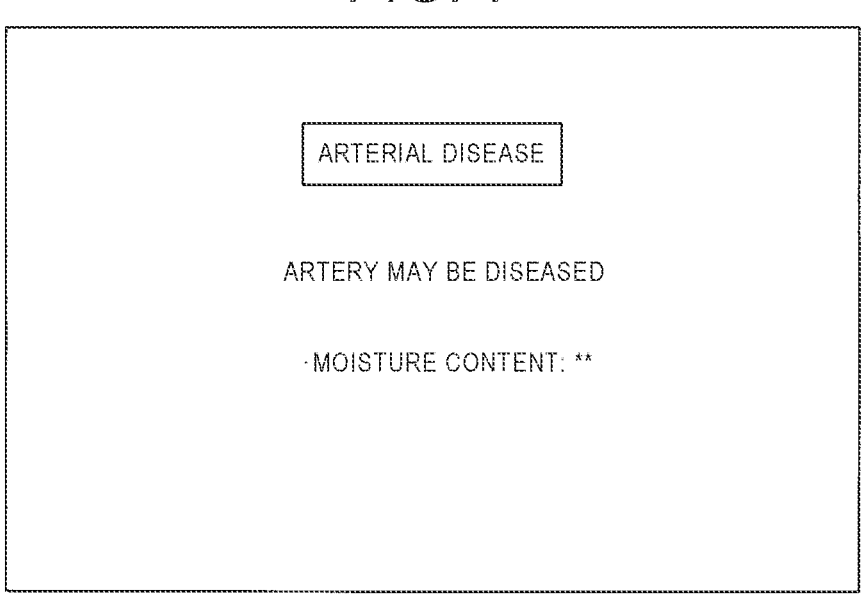
FIG. 7 is a schematic diagram illustrating a screen image showing information on a risk of an arterial disease and a venous disease of a leg of a person.

FIG. 7 is a schematic diagram illustrating an output example of a screen image showing the information on the risk of the arterial disease and the venous disease of the leg of the person 4 on the display unit 26. The information indicating which of the artery and the vein of the leg of the person 4 is diseased is included in the image and output. When it is determined that the artery of the leg of the person 4 is diseased, a message indicating that the artery is diseased is output. When it is determined that the vein of the leg of the person 4 is diseased, a message indicating that the vein is diseased is output. When it is determined that neither the artery nor the vein is diseased, a message indicating that neither the artery nor the vein is diseased is output. FIG. 7 illustrates an example in which the artery is diseased. When the degree of disease is determined, the calculation unit 21 controls the display unit 26 to display a message or an image indicating the degree of disease. Both a possibility that the artery of the leg of the person 4 is diseased and a possibility that the vein is diseased may be output. For example, when it is determined that the artery of the leg of the person 4 is diseased, a message or an image indicating the possibility that the artery is diseased is high and the possibility that the vein is diseased is low is displayed on the display unit 26.

The information output device 1 executes processing of outputting information on a body of the person 4 obtained by using the sensor device 3. In S14, the information output device 1 transmits the measurement information to the terminal device 2, and the terminal device 2 displays an image including a value indicated by the measurement information on the display unit 26. FIG. 7 illustrates an example in which the moisture content contained in the leg of the person 4 is output. The repulsive force, the color of skin, and/or the hemoglobin amount may be output.

The information output device 1 may execute processing for outputting a disease treatment policy in addition to the information indicating which of the artery and the vein of the leg of the person 4 is diseased or whether neither the artery nor the vein is diseased. For example, the information output device 1 stores a treatment database in which the disease treatment policy is recorded in association with each of the arterial disease and the venous disease in the storage unit 13 in advance. In S14, the information output device 1 reads the treatment policy in association with the determined disease from the treatment database, and outputs the treatment policy. A message or an image indicating the treatment policy in addition to the information indicating which of the artery and the vein of the leg of the person 4 is diseased or whether neither the artery nor the vein is diseased is displayed on the display unit 26 of the terminal device 2. For example, when the disease is the arterial disease, a treatment policy of recommending use of an atherectomy device is output, and when the disease is the venous disease, a treatment policy of recommending use of a thrombus disruption device is output.

After S14 is ended, the information output system 100 ends the process of outputting the information on the risk of the arterial disease and the venous disease of the leg of the person 4. The information output system 100 executes the process of S11 to S14 at any time. The user such as a health care worker can confirm the information on the risk of the arterial disease and the venous disease of the leg of the person 4 using the terminal device 2. For example, the user can know which of the artery and the vein of the leg of the person 4 is diseased. Alternatively, the user can know that neither the artery nor the vein of the leg of the person 4 is diseased.

As described above in detail, the information output device 1 acquires the measurement information on the state of the leg of the person 4 using the sensor device 3, and determines the risk of the arterial disease and the venous disease of the leg of the person 4 based on the measurement information. In addition, the information output device 1 outputs the information on the determined risk of the arterial disease and the venous disease of the leg of the person 4 using the terminal device 2. It is possible to easily determine and notify of the risk of the arterial disease and the venous disease of the leg of the person 4 by attaching the sensor device 3 to the leg of the person 4. It is possible to easily determine which of the artery and the vein is diseased or whether neither the artery nor the vein is diseased, and it is possible to execute a more precise examination on a blood vessel that is determined as being diseased. Since the determination is easy to be executed, it is possible to detect the arterial disease or the venous disease of the leg of the person 4 at an early stage.

In the present embodiment, the moisture content contained in the leg of the person 4, the repulsive force generated from the leg when the pressure is applied to the skin of the leg, the color of skin of the leg, or the hemoglobin amount in the leg is used as the measurement information. Thus, it is possible to determine whether the artery of the leg is diseased or the vein is diseased based on the moisture content, the repulsive force, the color of skin, and/or the hemoglobin amount.

In the present embodiment, the information output device 1 acquires the angular velocity information using the gyro sensor 34, determines whether the person 4 is standing using angular velocity information, and determines the risk of the arterial disease and the venous disease of the leg when the person 4 is not standing. Swelling is more likely to appear in the leg when the person 4 is not standing, such as in a state in which the person 4 is sitting, than when the person 4 is standing, and a difference between a case in which the vein of the leg is diseased and a case in which the vein is not diseased is more easily to appear. Therefore, it is possible to correctly determine the risk of the arterial disease and the venous disease of the leg of the person 4.

Second Embodiment

Figure 8:
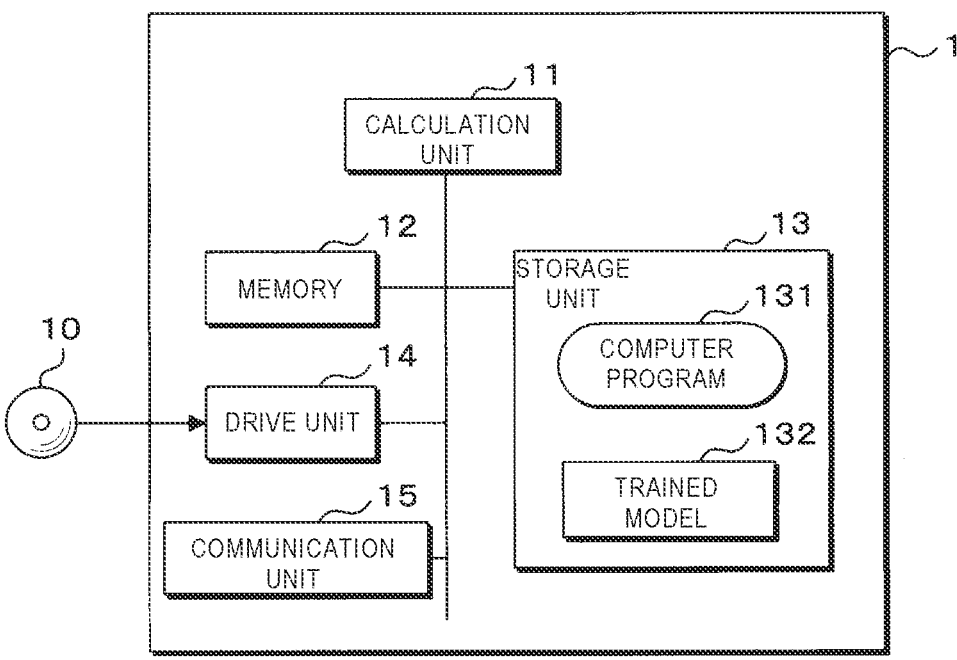
FIG. 8 is a block diagram illustrating an internal functional configuration of an information output device according to a second embodiment.

FIG. 8 is a block diagram illustrating an internal functional configuration of an information output device 1 according to a second embodiment. The information output device 1 includes a trained model 132 used to determine a risk of an arterial disease and a venous disease of a leg of the person 4 based on measurement information. The trained model 132 is implemented by software such as a computer program 131 executed by the calculation unit 11. The storage unit 13 stores data necessary for using the trained model 132. Alternatively, the trained model 132 may be implemented by hardware such as a dedicated circuit. The trained model 132 may be executed by a quantum processor. The trained model 132 may be provided outside the information output device 1, and the information output device 1 may execute processing using the external trained model 132. Configurations and functions of other portions of the information output device 1 are the same as those in the first embodiment. In addition, configurations and functions of units other than the information output device 1 of the information output system 100 are the same as those in the first embodiment.

Figures 9, 10:
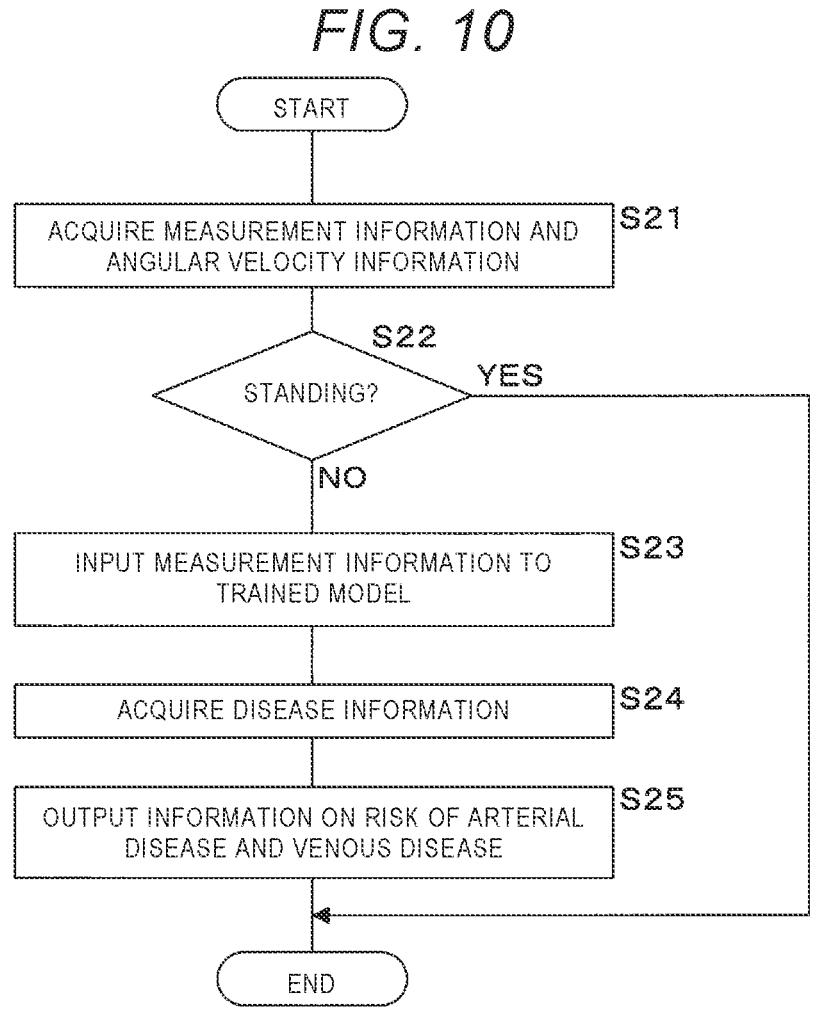
FIG. 9 is a schematic diagram illustrating functions of a trained model.
FIG. 10 is a flowchart of an information output process executed by an information output system according to the second embodiment.

FIG. 9 is a schematic diagram illustrating functions of the trained model 132. The measurement information is input to the trained model 132. The trained model 132 is trained in advance so as to output disease information on the risk of the arterial disease and the venous disease of the leg of the person 4 when the measurement information is input. For example, the disease information indicates a probability that an artery of the leg of the person 4 is diseased and a probability that a vein is diseased. For example, the trained model 132 is implemented by a neural network such as a convolutional neural network (CNN), a long short-term memory (LSTM), or a transformer. The trained model 132 may be a model using a method other than the neural network.

The trained model 132 is generated by machine learning using training data including the measurement information such as a moisture content, a repulsive force, a color of skin, or a hemoglobin amount obtained in the past, and a result of a medical examination performed on a leg of a person in the past. For example, the measurement information obtained regarding the leg of the person is associated with the disease information on the risk of the arterial disease and the venous disease, which is the result of the examination related to the leg, and the training data including a plurality of sets of the associated measurement information and disease information is used. The machine learning is executed by an information processing device.

In the machine learning, the measurement information is input to a model that is a basis of the trained model 132, and the model calculates according to the input of the measurement information and outputs the disease information. For example, the disease information indicates the probability that the artery is diseased and the probability that the vein is diseased. The information processing device that executes the machine learning adjusts parameters of the calculation of the model such that an error between the disease information output by the model and the disease information associated with the input measurement information is reduced. That is, the parameters are adjusted such that the probability that the artery is diseased and the probability that the vein is diseased, which are indicated by the disease information associated with the measurement information, substantially match the probability that the artery is diseased and the probability that the vein is diseased, which are indicated by the output disease information.

The information processing device executes the machine learning by repeating processing using the plurality of sets of the measurement information and the disease information included in the training data and adjusting the parameters of the model. By adjusting the parameters of the calculation in this way, the trained model 132 is generated. For example, adjusted final parameters are stored in the storage unit 13, and the trained model 132 is executed by the calculation unit 11 using those parameters.

FIG. 10 is a flowchart of an information output process executed by the information output system 100 according to the second embodiment. As in the first embodiment, the information output device 1 acquires the measurement information and the angular velocity information (S21). As in the first embodiment, the information output device 1 determines whether the person 4 is standing based on the angular velocity information (S22). When the person 4 is standing (S22: YES), the information output device 1 ends the process.

When the person 4 is not standing (S22: NO), the information output device 1 inputs the measurement information to the trained model 132 (S23). Specifically, in S23, the calculation unit 11 uses the measurement information as an input to the trained model 132, and acquires its output, i.e., the disease information on the risk of the arterial disease and the venous disease of the leg of the person 4 corresponding to the input measurement information (S24). In S24, the calculation unit 11 determines the risk of the arterial disease and the venous disease of the leg of the person 4 by acquiring the disease information. For example, by obtaining the probability that the artery of the leg of the person 4 is diseased and the probability that the vein is diseased indicated by the disease information, which of the artery and the vein is diseased or whether neither the artery nor the vein is diseased is determined. That is, it is determined that one of the artery and the vein having a higher probability of being diseased is diseased. Alternatively, when both the probability that the artery is diseased and the probability that the vein is diseased are low, it is determined that neither the artery nor the vein is diseased.

The information output device 1 may determine the risk of the arterial disease and the venous disease of the leg of the person 4 based on the measurement information measured a plurality of times. For example, an average value of a plurality of pieces of the measurement information acquired within a predetermined length of time is input to the trained model 132. For example, the trained model 132 is trained in advance so as to output the disease information when time series of the measurement information are input. In this aspect, in S23, the calculation unit 11 inputs the time series of the measurement information to the trained model 132.

The information output device 1 may determine the risk of the arterial disease and the venous disease of the leg of the person 4 also using the angular velocity information in addition to the measurement information. In this aspect, the trained model 132 is trained in advance so as to output the disease information when the angular velocity information is input in addition to the measurement information. In this aspect, the processing of S22 is omitted, and determination according to whether the person 4 is standing may be executed.

In S23, the measurement information indicating any one type of measurement information, such as a moisture content, a repulsive force, a color of skin, or a hemoglobin amount may be used, and a plurality of types of such measurement information may be used. In an aspect in which the plurality of types of measurement information are used, the trained model 132 is trained in advance so as to output the disease information when the plurality of types of measurement information are input. In S23, the calculation unit 11 inputs the plurality of types of measurement information to the trained model 132.

The information output device 1 may determine the risk of the arterial disease and the venous disease of the leg of the person 4 according to a medical history of the person 4. In this aspect, the trained model 132 is trained in advance so as to output the disease information on the risk of the arterial disease and the venous disease of the leg of the person 4 when the medical history of the person 4 is input in addition to the measurement information. In S23, the calculation unit 11 identifies the medical history of the person 4 in the same manner as in the first embodiment, and inputs the identified medical history and the measurement information to the trained model 132. The trained model 132 outputs the disease information according to the input of the measurement information and the medical history.

After S24 is ended, the information output device 1 outputs the information on the risk of the arterial disease and the venous disease of the leg of the person 4 according to the state information (S25). In S25, the calculation unit 11 controls the communication unit 15 to transmit the disease information to the terminal device 2. The terminal device 2 receives the disease information via the communication unit 27. The calculation unit 21 controls the display unit 26 to display a message or an image showing the risk of the arterial disease and the venous disease of the leg of the person 4 indicated by the disease information. In S25, the calculation unit 11 may generate image data representing the image including the information on the risk of the arterial disease and the venous disease of the leg according to the disease information, and control the terminal device 2 to transmit the image data to the terminal device 2. The terminal device 2 may display the image including the information on the risk of the arterial disease and the venous disease of the leg on the display unit 26 based on the image data. In S25, a message or an image similar to that of the first embodiment is displayed. That is, information indicating which of the artery and the vein of the leg of the person 4 is diseased is output. When it is determined that neither the artery nor the vein is diseased, a message or an image indicating that neither the artery nor the vein is diseased is output. The message or image displayed in S25 may include the probability that the artery of the leg of the person 4 is diseased and the probability that the vein is diseased.

After S25 is ended, the information output system 100 ends the information output process of outputting the information on the risk of the arterial disease and the venous disease of the leg of the person 4. The information output system 100 executes the process of S21 to S25 at any time.

As described above in detail, in the second embodiment, the information output device 1 uses the trained model 132 to output the information on the risk of the arterial disease and the venous disease of the leg of the person 4 according to the measurement information. By using the trained model 132, it is possible to easily determine the risk of the arterial disease and the venous disease of the leg of the person 4. In the second embodiment, it is also possible to easily determine whether the artery of the leg of the person 4 is diseased or the vein is diseased, and it is possible to execute a more precise examination when it is determined that the artery or the vein is diseased. Since the determination is easy to be executed, it is possible to detect the arterial disease or the venous disease of the leg of the person 4 at an early stage.

Third Embodiment

Figure 11:
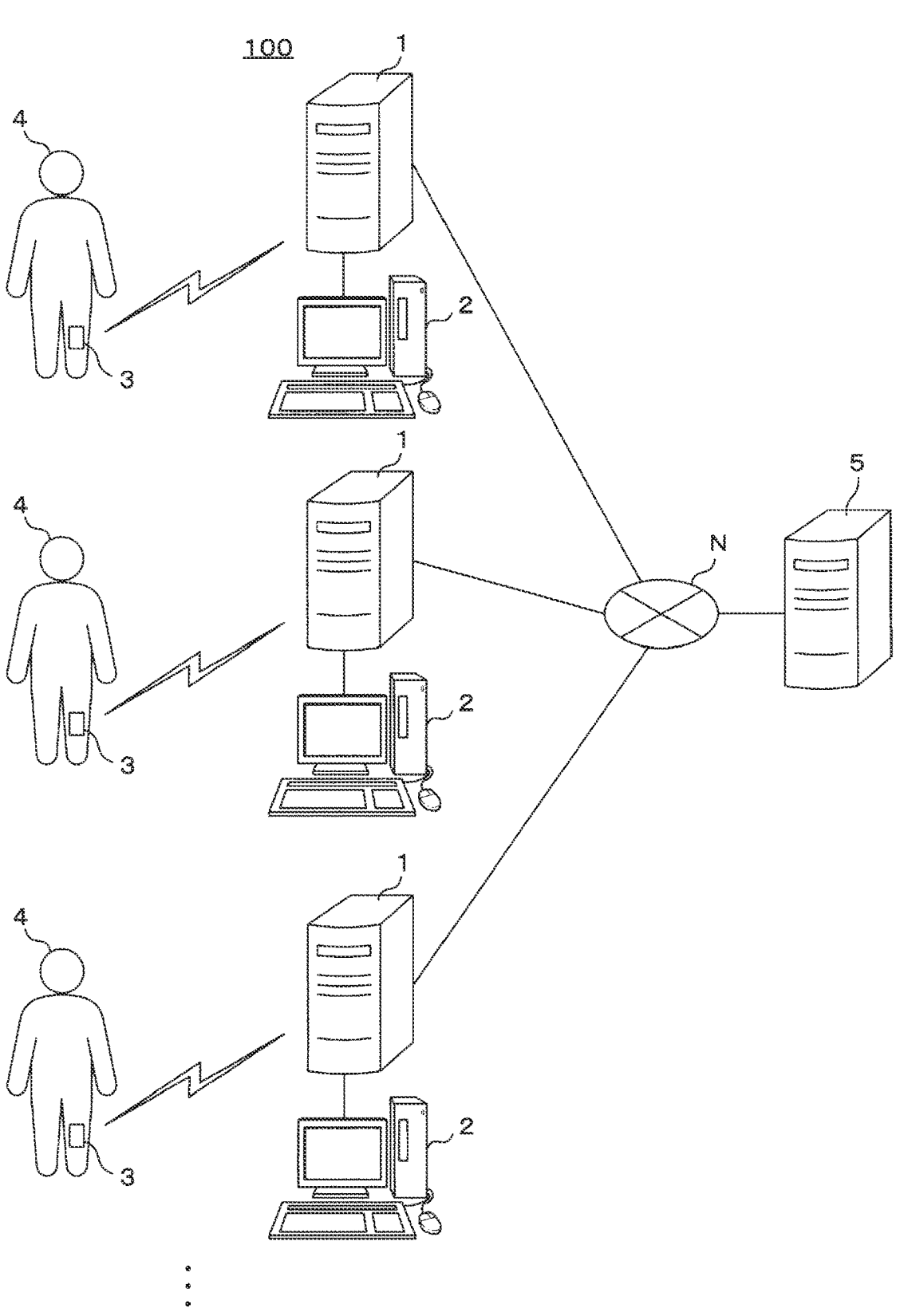
FIG. 11 is a schematic diagram illustrating a configuration of an information output system according to a third embodiment.

FIG. 11 is a schematic diagram illustrating a configuration of an information output system 100 according to a third embodiment. The information output system 100 includes a plurality of sets of the information output device 1, the terminal device 2, and the sensor device 3. A plurality of information output devices 1 are connected to the communication network N such as the Internet. The information output system 100 further includes a storage device 5. The storage device 5 is connected to the communication network N. The information output device 1 uses the communication unit 15 to communicate with the storage device 5 via the communication network N.

Figure 12:
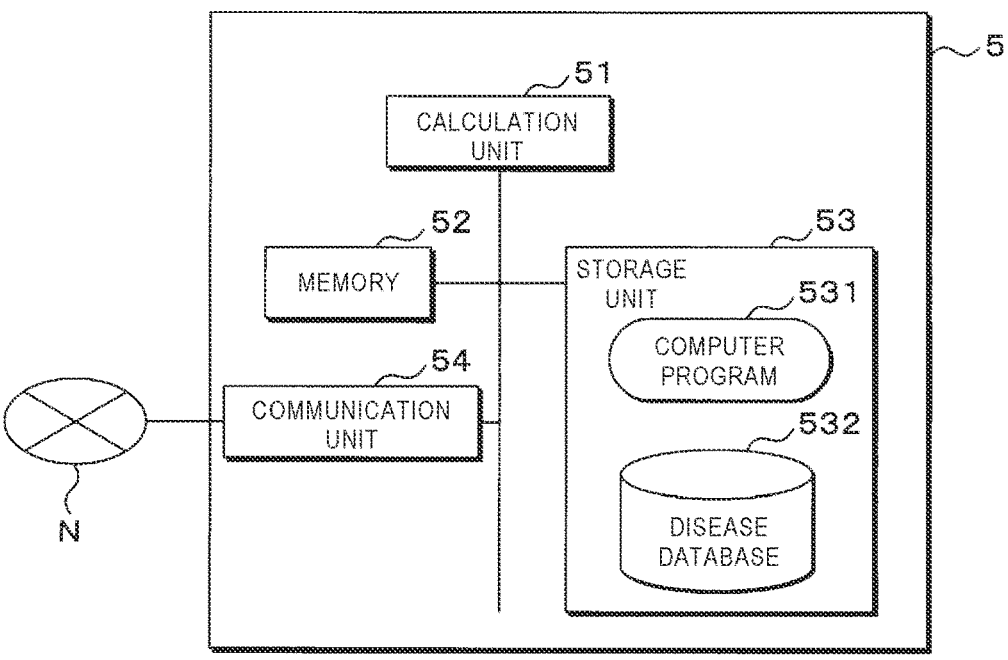
FIG. 12 is a block diagram illustrating an internal functional configuration of a storage device.

FIG. 12 is a block diagram illustrating an internal functional configuration of the storage device 5. The storage device 5 is a computer such as a compute server. The storage device 5 includes a calculation unit 51, a memory 52 that stores temporary data generated along with calculation, a storage unit 53, and a communication unit 54. The calculation unit 51 is a processor, such as a CPU, a GPU, or a multi-core CPU. The calculation unit 51 may be a quantum processor. The memory 52 is, for example, a RAM. The communication unit 54 is a network interface circuit connected to the communication network N. The communication unit 54 communicates with the information output device 1 via the communication network N.

The storage unit 53 is nonvolatile, and is, for example, a hard disk drive. The storage unit 53 stores a computer program 531. The calculation unit 51 executes processing necessary for the storage device 5 according to the computer program 531. In addition, the storage unit 53 stores a disease database 532 in which measurement information and information on a risk of an arterial disease and a venous disease of a leg of the person 4 are recorded in association with each other. The storage device 5 may be implemented by a plurality of computers.

The information output system 100 according to the third embodiment executes an information output method in the same manner as in the first embodiment or the second embodiment. That is, the storage unit 13 of the information output device 1 stores threshold data in advance, and the information output system 100 executes the process of S11 to S14. Alternatively, the information output device 1 uses the trained model 132, and the information output system 100 executes the process of S21 to S25.

Figure 13:
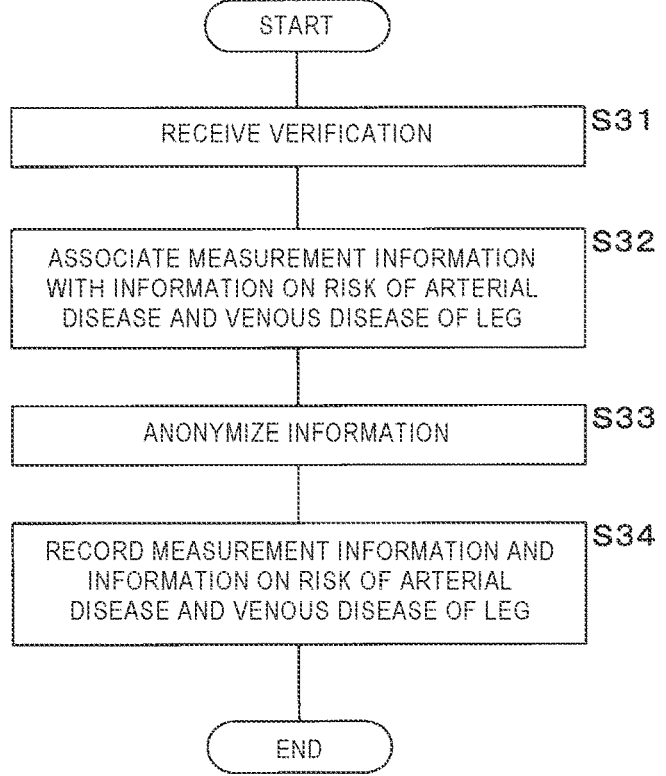
FIG. 13 is a flowchart of an information record process executed by the information output system according to the third embodiment.

After the process of S11 to S14 or S21 to S25 is executed, the information output system 100 executes an information record process of recording the measurement information and the information on the risk of the arterial disease and the venous disease of the leg of the person 4. FIG. 13 is a flowchart of the information record process executed by the information output system 100 according to the third embodiment. The information output system 100 receives verification on the measurement information and the information on the risk of the arterial disease and the venous disease of the leg of the person 4 from a health care worker such as a doctor (S31).

The user who is a health care worker confirms the measurement information and the information on the risk of the arterial disease and the venous disease of the leg of the person 4 output using the terminal device 2. In S31, the user inputs a verification result of the measurement information and the information on the risk of the arterial disease and the venous disease of the leg of the person 4 by operating the operation unit 25. For example, when no discrepancy is present in correlation between the measurement information and the information on the risk of the arterial disease and the venous disease of the leg of the person 4, the user inputs a verification result indicating that no problem is present to the terminal device 2. For example, the user inputs correction of the information on the risk of the arterial disease and the venous disease of the leg of the person 4 as the verification result as necessary. The terminal device 2 transmits the verification result from the communication unit 27 to the information output device 1. The information output device 1 receives the verification by receiving the verification result via the communication unit 15.

The information output device 1 associates the information on the risk of the arterial disease and the venous disease of the leg of the person 4 with the measurement information (S32). In S32, the calculation unit 11 associates the measurement information acquired in the process of S11 to S14 or S21 to S25 with the information on the risk of the arterial disease and the venous disease of the leg of the person 4, which is determined and verified based on the measurement information. The calculation unit 11 may also associate information other than the measurement information such as a medical history with the information on the risk of a disease.

Next, the information output device 1 anonymizes the information (S33). In S33, the calculation unit 11 anonymizes information related to the person 4, which is included in the measurement information and the information on the risk of the arterial disease and the venous disease of the leg of the person 4, such that the person 4 cannot be identified (e.g., by replacing the sensor ID or user ID with a random number). For example, the calculation unit 11 deletes personal information included in the measurement information and the information on the risk of the arterial disease and the venous disease of the leg of the person 4 or replaces the personal information with information by which the person 4 cannot be identified.

The information output device 1 records the anonymized measurement information and information on the risk of the arterial disease and the venous disease of the leg of the person 4 (S34). In S34, the calculation unit 11 causes the communication unit 15 to transmit the measurement information and the information on the risk of the arterial disease and the venous disease of the leg of the person 4, which are in association with each other and are anonymized, to the storage device 5 via the communication network N. The storage device 5 receives the information transmitted from the information output device 1 via the communication unit 54. The calculation unit 51 records the received measurement information and information on the risk of the arterial disease and the venous disease of the leg of the person 4 in the disease database 532 in association with each other. In S33, anonymization may be executed so that the person 4 cannot be identified but the person 4 is the same person, and in S34, information on the same person may be collectively recorded. For example, information acquired a plurality of times for the same person is collectively recorded.

After S34 is ended, the information output system 100 ends the information record process. The process of S31 to S34 is executed at any time using a plurality of information output devices 1, terminal devices 2, and sensor devices 3, and information on a plurality of persons 4 is recorded in the disease database 532. The information recorded in the disease database 532 is used, for example, as training data for generating the trained model 132 by machine learning.

As described above in detail, in the third embodiment, the information output system 100 determines the risk of the arterial disease and the venous disease of the leg of the person 4, outputs the information on the risk of the arterial disease and the venous disease, and records the measurement information and the information on the risk of the arterial disease and the venous disease in the disease database 532. The recorded information can be utilized for future medical diagnoses. For example, it is possible to generate and improve the trained model 132 by machine learning using the information recorded in the disease database 532 as the training data and to correctly determine the risk of the arterial disease and the venous disease of the leg of the person 4 using the trained model 132.

In the first to third embodiments, the information output system 100 is used for an examination in a medical facility such as a clinic or a hospital, while the information output system 100 may be used outside the medical facility. For example, the sensor device 3 may be always attached to the person 4, and the risk of the arterial disease and the venous disease of the leg of the person 4 may be routinely determined. For example, the terminal device 2 is a property of the person 4, and the person 4 confirms the information on the risk of the arterial disease and the venous disease of the leg using the terminal device 2.

The information output device 1 may determine the risk of the arterial disease and the venous disease of the leg of the person 4 based on the measurement information acquired in an identified time zone. Swelling is more likely to appear in a morning time zone than in a daytime zone or a nighttime zone, and a difference between a case in which the vein of the leg is diseased and a case in which the vein is not diseased is more likely to appear. Therefore, the information output device 1 can correctly determine the risk of the arterial disease and the venous disease of the leg of the person 4 by determining based on measurement information acquired in the morning time zone.

In the first to third embodiments, the information on the risk of the arterial disease and the venous disease of the leg of the person 4 is displayed on the terminal device 2, while the information output system 100 may also display the information on an information processing device other than the terminal device 2. For example, the information is displayed on a terminal device used by the person 4 other than the terminal device 2 used by the health care worker. In the first to third embodiments, the gyro sensor 34 is used, while the information output system 100 may not use the gyro sensor 34. For example, in the process of S11 to S14 or S21 to S25, processing in which processing using the angular velocity information is omitted may be executed. In the first to third embodiments, the sensor device 3 is attached to the leg of the person 4 outside a medical facility such as a clinic or a hospital. Alternatively, the sensor device 3 may be used in such a medical facility, and measure information on a state of a leg of a person in a non-contact manner.

The invention is not limited to the above-described embodiments, and various modifications can be made within the scope of the claims. That is, embodiments obtained by combining technical means appropriately modified within the scope of the claims are also included in the technical scope of the invention.

What is claimed is:

1. A system for monitoring a health status of a person remotely from a medical facility, comprising:
   a display device at the medical facility;

a wireless sensor device attachable to a surface of a leg of the person to acquire measurement information on a state of the leg of the person that is measurable only from the surface of the leg, the sensor device including a moisture sensor and the measurement information indicating a moisture content of the leg; and
   a compute server in wireless communication with the sensor device to acquire the measurement information, wherein
   the compute server is configured to:
      compare the moisture content to a first threshold and a second threshold that is greater than the first threshold,
      determine that there is a risk of an arterial disease of the leg when the moisture content is below the first threshold,
      determine that there is a risk of a venous disease of the leg when the moisture content is above the second threshold,
      determine that there is no risk of arterial and venous diseases when the moisture content is greater than or equal to the first threshold and is smaller than or equal to the second threshold, and
      output, to the display device, information on the determined risk regarding arterial and venous diseases of the leg.

2. The system according to claim 1, wherein the sensor device includes a repulsive force sensor that measures a repulsive force received from the leg when pressure is applied to skin of the leg, and the measurement information further indicates the measured repulsive force.

3. The system according to claim 2, wherein the sensor device further includes a belt by which the pressure can be applied to the skin of the leg.

4. The system according to claim 1, wherein the sensor device includes a color sensor that measures a color of skin of the leg, and the measurement information further indicates the measured color.

5. The system according to claim 4, wherein the compute server is further configured to:
   determine that there is a risk of the arterial disease when the color of the skin measured by the color sensor is whiter than a first standard color, and
   determine that there is a risk of the venous disease when the color of the skin measured by the color sensor is darker red than a second standard color that is different from the first standard color.

6. The system according to claim 1, wherein the sensor device includes an infrared sensor that measures a hemoglobin amount in a blood vessel of the leg according to an absorption amount of infrared rays radiated to skin of the leg.

7. The system according to claim 1, wherein
   the sensor device further includes a repulsive force sensor that measures a repulsive force received from the leg when pressure is applied to skin of the leg, a color sensor that measures a color of skin of the leg, and an infrared sensor that measures a hemoglobin amount in a blood vessel of the leg according to an absorption amount of infrared rays radiated to the skin of the leg, and
   the measurement information further indicates the repulsive force, the color of the skin, and the hemoglobin amount.

8. The system according to claim 1, wherein
   the sensor device includes a gyro sensor that is configured to acquire angular velocity information, and the compute server is further configured to:

acquire, from the sensor device, the measurement information and the angular velocity information, determine whether the person is standing based on the angular velocity information, and in response to determining that the person is not standing, determine the risk of the arterial disease and the venous disease based on the measurement information, and output the information on the determined risk.

9. The system according to claim 1, wherein the compute server is further configured to use a machine learning model that has been trained to determine the risk of the arterial disease and the venous disease of the leg corresponding to the measurement information.

10. The system according to claim 1, wherein the compute server is further configured to:

acquire information indicating a medical history of the person, and determine the risk of the arterial disease and the venous disease of the leg further based on the medical history of the person.

11. The system according to claim 1, wherein the compute server is further configured to store in a database the information on the risk of the arterial disease and the venous disease of the leg in association with the measurement information so as not to include personal information of the person.

12. The system according to claim 1, wherein the compute server is configured to determine the risk of the arterial disease and the venous disease of the leg based on the moisture content measured during a morning time period.

13. The system according to claim 1, wherein the compute server is further configured to:

store a treatment database in which a disease treatment policy is recorded in association with each of the arterial disease and the venous disease, read the treatment policy associated with the determined risk from the treatment database, and output the read treatment policy to the display device.

14. A non-transitory computer readable medium storing a program for monitoring a health status of a person remotely from a medical facility, wherein the program executed on a computer causes the computer to execute a method comprising:

acquiring, from a wireless sensor device attached to a surface of a leg of the person, measurement information on a state of the leg of the person that is measurable only from the surface of the leg, the sensor device including a moisture sensor and the measurement information indicating a moisture content of the leg;

comparing the moisture content to a first threshold and a second threshold that is greater than the first threshold;

determining that there is a risk of an arterial disease of the leg when the moisture content is below the first threshold;

determining that there is a risk of a venous disease of the leg when the moisture content is above the second threshold;

determining that there is no risk of arterial and venous diseases when the moisture content is greater than or equal to the first threshold and is smaller than or equal to the second threshold; and outputting, to a display device installed in the medical facility, information on the determined risk regarding arterial and venous diseases of the leg.

15. The computer readable medium according to claim 14, wherein the measurement information further indicates a repulsive force received from the leg when pressure is applied to skin of the leg.

16. The computer readable medium according to claim 15, wherein the pressure is applied to the skin of the leg by a belt of the sensor device.

17. The computer readable medium according to claim 14, wherein the measurement information indicates a color of skin of the leg.

18. The computer readable medium according to claim 14, wherein the measurement information indicates a hemoglobin amount in a blood vessel of the leg.

19. The computer readable medium according to claim 14, wherein the method further comprises:

acquiring, from the sensor device, angular velocity information; and determining whether the person is standing based on the angular velocity information, wherein in response to determining that the person is not standing, the risk of the arterial disease and the venous disease is determined based on the measurement information, and then the information on the determined risk is output to the display device.

20. A method of monitoring a health status of a person remotely from a medical facility, the method comprising:

acquiring, from a wireless sensor device attached to a surface of a leg of the person, measurement information on a state of the leg of the person that is measurable only from the surface of the leg, the sensor device including a moisture sensor and the measurement information indicating a moisture content of the leg;

comparing the moisture content to a first threshold and a second threshold that is greater than the first threshold;

determining that there is a risk of an arterial disease of the leg when the moisture content is below the first threshold;

determining that there is a risk of a venous disease of the leg when the moisture content is above the second threshold;

determining that there is no risk of arterial and venous diseases when the moisture content is greater than or equal to the first threshold and is smaller than or equal to the second threshold; and outputting, to a display device installed in the medical facility, information on the determined risk regarding arterial and venous diseases of the leg.

* * * * *